(12) United States Patent
Hippenmeyer et al.

(10) Patent No.: US 6,635,478 B1
(45) Date of Patent: Oct. 21, 2003

(54) PRODUCTION OF RECOMBINANT PROTEINS USING HERPES VIRUS PROMOTERS AND VP16 TRANSACTIVATORS

(75) Inventors: Paul Jerome Hippenmeyer, St. Louis, MO (US); Maureen Katherine Highkin, St. Louis, MO (US)

(73) Assignee: G. D. Searle & Co., Chicago, IL (US)

( * ) Notice: Subject to any disclaimer, the term of this patent is extended or adjusted under 35 U.S.C. 154(b) by 1705 days.

(21) Appl. No.: 08/641,294

(22) Filed: Apr. 30, 1996

Related U.S. Application Data (63) Continuation of application No. 08/290,050, filed on Aug. 15, 1994, now abandoned, which is a continuation of application No. 07/850,700, filed on Mar. 13, 1992, now abandoned.

(51) Int. Cl.[7] .......................... C12N 5/16; C12N 15/79; C12N 15/85
(52) U.S. Cl. .................. 435/325; 435/69.1; 435/69.2; 435/69.4; 435/69.6; 435/69.7; 435/69.8; 435/352; 435/358; 435/455; 435/465
(58) Field of Search ............................ 435/69.1, 69.2, 435/69.4, 69.6, 69.7, 69.8, 70.1, 70.3, 171.1, 172.3, 325, 212, 226, 229, 6, 455, 465, 358, 352; 935/23, 32, 34, 43, 70

(56) References Cited

U.S. PATENT DOCUMENTS

| | | | | | |
|---|---|---|---|---|---|
| 4,738,922 A | * | 4/1988 | Hazeltine et al. | ........... | 435/69.3 |
| 4,740,461 A | * | 4/1988 | Kaufman | ................ | 435/69.1 |
| 5,026,635 A | * | 6/1991 | Ferguson et al. | .............. | 435/5 |

FOREIGN PATENT DOCUMENTS

| | | | |
|---|---|---|---|
| EP | 0282330 | * | 9/1988 |
| EP | 0291893 | * | 11/1988 |
| EP | 0327960 | * | 8/1989 |
| EP | 378382 | | 7/1990 |
| EP | 455424 | | 11/1991 |
| WO | 9101379 | * | 2/1991 |

OTHER PUBLICATIONS

Post et al. Cell 1981 24:555–565.*
Werstuck et al., J. Virology 1990 64: 984–991.*
Liu et al. Biotechniques 1990 9:168–173.*
Weinheimer et al J. Virol 1992 66:258–269.*
Hsu et al., Science (1991) 254: 1799–1802.*
Foecking, et al., Gene (1986) 45: 101–105.*
Hippenmeyer et al., Poultry Science (1991) 70:982–992.*
Silver et al., Molecular and Cellular Biology (1985) 5:518–528.*
Kmetz et al. Nucleic Acid Research (1988) 16:4725.*
Bercand et al. 1988 Nucleic Acid Res. 16(24):11573–11590.*
Yoshimura et al. 1987. Mol. Cell. Biol. 7(3): 1296–1299.*
Stabell et al. 1992. J. Virological Methods. 38:195–204.*
Israel et al., "Highly Inducible Expression from vectors containing . . ." Nuc. Acids Res., 17 (1989) pp. 4589–4604.

\* cited by examiner

*Primary Examiner*—Scott D. Priebe
(74) *Attorney, Agent, or Firm*—Verne A. Luckow (57) ABSTRACT

Stable cell lines are produced to express high levels of a gene product of interest using VP16, a herpes simplex virus transactivator, and a promoter from herpes simplex virus which is a target for VP16. The transactivator and promoter are introduced to a cell line separately using antibiotic resistance genes as selectable markers on separate vectors.

20 Claims, 4 Drawing Sheets

PRODUCTION OF RECOMBINANT PROTEINS USING HERPES VIRUS PROMOTERS AND VP16 TRANSACTIVATORS

This is a file-wrapper-continuation, of application Ser. No. 08/290,050 filed Aug. 15, 1994, now abandoned, which is a file-wrapper-continuation of application Ser. No. 07/850,700 filed Mar. 13, 1992, now abandoned.

BACKGROUND OF THE INVENTION

1. Field of the Invention

This invention pertains to production of recombinant proteins and more particularly to a means of heterologous gene transactivation.

2. Related Art

The ability to efficiently produce recombinant proteins in mammalian cell culture is critical for the production of both research agents and commercial products. Several approaches and host vector systems for the production of recombinant proteins have been reviewed (Kaufman, *Genetic Engineering, Principles and Methods*, vol. 9, J. K, Setlow, ed., Plenum Press, New, York, 1987; Warren et al., *Recombinant DNA Technology and Applications*, A. Prokop, R. Bajpai and C. Ho, eds., McGraw Hill, New York, 1990). These systems include use of high copy episomal vectors such as bovine papillomavirus (Howley et al., *Methods in Enzymology*, vol. 101, Academic Press, New York, 1983), amplifiable vectors such as those containing the dihydrofolate reductase gene (Kaufman,supra), the asparagine synthetase gene (Andrulis, *Molecular Cell Genetics*, vol. 17, 1985) or the ornithine decarboxylase gene (McConlogue, *Gene Transfer Vectors for Mammalian Cells*. 1987) or strong constitutive promoters such as the simian virus 40 promoter (Mulligan et al., *Science.* vol. 209, pp. 1422–1427, 1980) or the human cytomegalovirus major early promoter (Boshart et al., *Cell*, vol. 41, pp. 521–530, 1985). All of these systems rely upon the levels of endogenous transactivators in the particular cell type to stimulate transcription of the promoters used to construct the expression vectors.

An alternative approach to high level production would be to engineer cells with a specific transcriptional activator or transactivator. If the transactivator has a specific target promoter, then the target promoter can be linked to a gene of interest and inserted into the engineered cell. The amount of target protein produced from that cell would depend on several parameters. First, the inherent specific activity of the transactivator will be a factor in the amount of transcription from the target promoter. In addition, the amount of transactivator produced by the target cell will affect the amount of transactivation. For instance, in Chinese hamster ovary cells (CHO) there is a low level of endogenous glucocorticoid receptor/transactivator present. Transfection of a plasmid that requires the glucocorticoid receptor/transactivator results in very little expression from that plasmid. However, if the cells are first engineered to express high levels of the glucocorticoid receptor/transactivator, then high level expression from the same plasmid is obtained (Israel et al., *Nuc. Acids Res.*, vol. 17, pp. 4589–4606, 1989). Therefore, the amount of transactivation depends on the amount of transactivator in the cell. The amount of transactivator will depend on the promoter used to drive expression of the transactivator and the site of the integration of the cassette in the host cell. Thirdly, the amount of target vector in a particular cell will influence how many copies will be transactivated. The site of integration of the target promoter may also play a role in the expression of the activated promoter.

Another important concern is the specificity of the transactivator. If the transactivator interacts with several endogenous cellular promoters, then it would be expected that those promoters will also be transactivated in the engineered host cell. This may or may not be a desired situation depending on what those genes are. A possible effect of using a promiscuous transactivator is that its binding to the endogenous promoters effectively lowers its free concentration in the cell, perhaps titrating out the amount available for transactivation of the targeted promoter.

Just because a promoter shows high level expression under transient conditions does not indicate that it will be useful for production of proteins under stable conditions. An example of which is the human cytomegalovirus (HCMV) immediate early (IE) promoter which is one of the strongest promoters used in the field for transient expression (Foecking et al., *Gene,* 45; pp. 101–145, 1986; Hippenmeyer et al., *Poultry Science* 70, pp. 982–992, 1991). In addition some viral genes do not have the expected regulation once integrated into the cell genome such as the thymidine kinase gene of herpes simplex virus (HSV) (Silver et al., *Molecular and Cellular Biology* 5; pp. 518–528, 1985).

Therefore, although E.P. application 8802149.5 shows that a cell line in which VP16 (also known as Vmw65, VF65 or alpha-TIF) is produced leads to transactivation of the target promoter under transient conditions and although Post et al, (*Cell* 24, pp. 555–565, 1981) showed that the immediate early (IE)175 promoter (also known as ICP4), when resident in the genome of a cell, can be transactivated by virus infection, neither show that when both VP16 and the target promoter operably linked to a gene of interest are integrated in the same cell that high level transactivation occurs and high level production of protein results.

There is a need in the art for cell lines and systems which can be used with a variety of genes to achieve stable, high level, recombinant protein production.

SUMMARY OF THE INVENTION

The invention contains a method of producing cell lines for high level expression of a gene product. The method comprises the steps of: cotransfecting a cell with a first construct which causes the cell to express herpes simplex virus transactivating protein VP16 and a second construct comprising a selectable resistance gene to a first selectable agent; selecting cells which are resistant to the first selectable agent; screening the cells which are resistant to the first selectable agent for cells which express VP16; cotransfecting the cell which expresses herpes simplex virus transactivating protein VP16 with third and fourth constructs, the third construct comprising herpes simplex virus gene promoter operably linked to a gene of interest, the fourth construct comprising a selectable resistance gene to a second selectable agent; selecting cells which are resistant to the second selectable agent; and screening cells which are resistant to the second selectable agent for expression of the gene product of said gene of interest.

In another embodiment of the invention are cell lines which express high levels of a gene product. The cell lines are made by the process of: cotransfecting a cell with a first construct which causes the cell to express herpes simplex virus transactivating protein VP16 and a second construct comprising a selectable resistance gene to a first antibiotic; selecting cells which are resistant to the first antibiotic, screening the cells which are resistant to the first antibiotic for cells which express VP16; cotransfecting the cell which expresses herpes simplex virus transactivating protein VP16 with third and fourth constructs, the third construct comprising a herpes simplex virus IE gene promoter operably linked to a gene of interest, the fourth construct comprising a selectable resistance gene to a second antibiotic; selecting cells which are resistant to the second antibiotic; and screening cells which are resistant to the second antibiotic for high expression of the gene product of said gene of interest.

Another embodiment of the invention in which a cell line expresses a high level of a gene product is provided. The cell lines comprise: a first construct which causes the cell to express herpes simplex virus transactivator protein VP16; a second construct comprising herpes simplex virus IE gene promoter operable linked to a gene of interest; a third and fourth construct each comprising a selectable resistance gene to an antibiotic.

In the above embodiments all types of herpes simplex virus IE promoters are intended, preferably from herpes simplex virus-1, preferably IE175 (also known as ICP4) or IE110 (also known as ICP0). The cell lines are preferably derived from baby hamster kidney (BHK-21) or Chinese Hamster Ovary (CHO-DUKX-B11 or DG44).

All types of VP16 are intended to be included in the invention but preferably VP16 from herpes simplex virus 1. The VP16 gene and protein from HSV-2 are anticipated to work as well as the VP16 gene and protein from HSV-1 due to the strong similarity in amino acid sequence between the two (Greaves et al *Journal of Virology* 65, pp. 6705–6713 1991; Cress et al *Gene*, 103, pp. 235–238, 1991).

The use of the cell lines in discovering compounds that interfere with the transactivation of the IE promoters of HSV by the VP16 molecule, is also intended. It is envisioned that a cell line that stably secretes a recombinant protein due to transactivation of an IE promoter by VP16 can be incubated with chemicals or natural products or unspecificied mixtures of chemicals or natural products. If the incubation of the cell with these compounds leads to a decrease in the amount of recombinant protein produced by the cell, then the compound is potentially acting at the VP16-mediated transactivation step of the recombinant protein expression. These compounds would then be tested to see if they interfere with the expression of a recombinant protein from a cell line in which expression was not under control of VP16. Those compounds that interfere with expression of the VP16-mediated transactivation and not expression in other-systems are potential anti-HSV agents.

It is anticipated that cell lines engineered to express VP16 will be useful for the passage and maintainence of mutants of HSV that lack a functional VP16 (Werstuck et al., *Journal of Virology*. vol. 64, pp. 984–991). The DNA of HSV which lacks a functional VP16 gene or protein can be transfected into a cell line that expresses VP16 from the integrated DNA constructs. The VP16 protein will transactivate the IE promoters of the HSV DNA leading to production of virus particles. Mutants of HSV that lack functional VP16 may be promising candidates for a vaccine strain.

The invention is intended to cover cell lines whether the cell lines secrete or do not secrete the gene product but preferably the cell lines secrete the gene product.

It is an object of the invention to provide a method of producing a cell line for high level expression of a gene product.

It is another object of the invention to provide cell lines which express a high level of a gene product.

It is still another object of the invention to provide the art with cell lines which can be used for the large scale production of any gene product of interest.

It is still another object of the invention to provide the art with means to propagate VP16-minus herpesvirus mutants.

It is still another object of the present invention to provide an assay for discovering anti-viral compounds.

It is an advantage of the invention to provide the art with stable cell lines that which can express a high level of a gene product for a period exceeding 5 months.

It is still another advantage of this invention in that a method is provided which allows isolating cell lines that produce higher expression levels of a gene product per cell per day faster than the art and the cell line is stable for a period exceeding 5 months. Many other objects and purposes of the invention will be clear from the following descriptions of the invention.

DETAILED DESCRIPTION OF THE PREFERRED EMBODIMENTS

It is a finding of the present invention that stable transfectants of mammalian cells with both a gene encoding a herpes simplex virus transactivator protein (VP16) and a herpes simplex virus gene promoter (IE promoter) linked to a gene of interest, can express the gene of interest to a high level. Particularly interesting is the fact that the specific way of constructing the cell lines can influence the outcome in unexpected ways. Whereas selections involving antibiotic resistance in CHO-DUKX-B11 cells have been found to be more successful, selections for dihydrofolate reductase expression in CHO-DUKX-B11 cells seem to be inimicable to obtaining the desired high producing cell lines.

The transactivator of herpes simplex virus is preferably the late viral protein known as VP16, VF65, Vmw65 or alpha-T1F. The target promoter for VP16 activation is preferably from the IE175 gene (also known as ICP4) of herpes simplex virus, although the IE110 promoter (also known as ICP0) may also be used. BHK-21 cells or dhfr-minus mutants of CHO such as CHO-DUKX-B11 or DG44, are preferred mammalian cells for the practice of this invention. These cells are well known in the art and widely available, for example, from the American Type Culture Collection, (A.T.C.C.) Rockville, Md. (BHK-21) or from Dr. Lawrence Chasin, Columbia University, New York (CHO DUKX-B11 or DG44). These cells adapt well to growth in suspension cultures and/or can grow under low serum concentrations. These qualities make them beneficial as large scale production strains for cellular products (Bendig, *Genetic Engineering*, vol. 7, P. W. Rigby, ed., Academic Press, pp. 91–127, 1988).

According to the present invention, DNA constructs are used to cotransfect cell lines. Cotransfection involves the introduction into a cell of at least two distinct DNA species. These may be linear or circular DNA molecules, viral or plasmid molecular segments of other larger molecules. Transfection can be accomplished by any means known in the art. Preferred methods include the calcium phosphate procedure (van der Eb et al., *Methods in Enzymology*, vol. 65, Gross and Moldave, eds., Academic Press, NY, 1980), and the use of "LIPOFECTIN"™ reagent (GIBCO-BRL) according to the manufacturer's instructions. Other techniques such as electroporation are also suitable (Chu et al., *Nucleics Acids Research*, vol. 15, 1311–1326, 1987).

Expression of the late viral protein, VP16, can be under the control of any promoter which is known in the art to be functional to initiate transcription in mammalian cells, particularly in CHO-dhfr-minus cells and BHK-21 cells. Particularly preferred promoters are the SV40 early promoter and the MMTV LTR.

Selectable antibiotic resistance genes include any which can function as positive selective markers in mammalian cells. Typically these are isolated from bacteria or yeast. A prerequisite is that the antibiotic (or an analog thereof) show some growth inhibitory activity toward mammalian cells. For example, "GENETICIN"™ (GIBCO, Division of Life Technologies, Inc.) (which is antibiotic G418), hygromycin-B (Blochlinger et al., *Molecular and Cellular Biology*, vol. 4, pp.2929–2931, 1984), bleomycin-phleomycin (Mulsant et al., *Somatic Cell Molecular Genetics*, vol. 14, pp.243–252, 1988) and puromycin (de la Luna et al., *Gene* vol. 62, pp.121–126, 1988) are inhibitory to eukaryotic cell growth. The resistance genes must be under the control of a suitable mammalian promoter so that they are efficiently expressed. According to the method of the present invention two different antibiotics are used to sequentially select cotransfected CHO-dhfr-minus cells or BHK-21 cells. That is to say that a first antibiotic is used to select cotransfection candidates expressing VP16 and a second antibiotic must be used to select cotransfection candidates expressing the gene of interest.

Cells which are resistant to the selective antibiotic are candidate cotransfectants. A cell which received one of the antibiotic resistant gene constructs is more likely than a cell which did not receive the antibiotic resistant gene construct to have received a second construct molecule. Screening for the second construct can be done by any means known in the art. Production of a product encoded by the second construct can be determined by various immunoassays (Harlow et al. *Antibodies: A Laboratory Manual*, pp. 553–612, Cold Spring Harbor Laboratory,1988), such as an ELISA, by enzymatic assay or other standard methods.

It is envisioned that other types of selectable agents besides antibiotics could be used as well [(MacDonald, *Critical Reviews in Biotechnology*, Vol. 10 pp 155–178, 1990), incorporated herein by reference]. However, the preferred selectable agents are antibiotics. It is also preferred that the DNA construct that encodes the antibiotic resistance gene is introduced by cotransfection into the mammalian cell but it is also intended that the antibiotic resistance gene, under a suitable eukaryotic promoter, can be linked to the IE promoter or VP16 constructs such that cotransfection is not required. This can be accomplished by using routine recombinant DNA techniques.

According to a preferred embodiment of the invention, a DNA construct encodes herpes simplex virus VP16. Cotransfectant candidates can be screened for VP16 production by Western blotting with anti-VP16 antisera. Other methods as are known in the art may also be used and are described below.

Any gene of interest may be put under the control of the HSV gene promoter IE175 or IE110. If the gene is placed downstream from the promoter without intervening transcription termination signals the gene is said to be operably linked to the promoter, and will be transcribed when transcription is initiated at the promoter.

High levels of expression of the gene of interest are a desirable goal of the invention. This is expression which is enhanced over the levels which are obtained in the absence of VP16 or a VP16-enhanceable promoter. It is desirable to collect as many of such high level expression transfectants as possible. These can be subsequently mutagenized, selected, engineered or treated with compounds to enhance the expression even further. For instance, if the expression constructs were cotransfected with a gene such that amplification of the transfected DNA is possible, higher levels of expression may be obtained (MacDonald, supra). Such amplification often leads to over-expression of genes which have been co-amplified.

It is possible that one could mutate the VP16 coding region such that the nucleotide sequence is changed but that the amino acid sequence is identical (due to degeneracy in the genetic code). It is also possible that deletions or substitutions in the amino acid sequence of VP16 could be made and VP16 would retain functional activity. Therefore, the invention is intended to include all functional forms of the VP16 gene and protein and derivatives thereof.

In the IE promoters of HSV it is known that the nucleotide sequence (TAATGARAT R=purine) is necessary for a functional transactivation of the IE genes by VP16. It is envisioned that a promoter containing only TAATGARAT, and not the rest of the sequences of an IE promoter can still be transactivated. The main targets of VP16 are the IE promoters of HSV-1 or 2; preferably IE-175 or IE-110 promoters. However, it is intended that other promoters, natural or synthetic, that respond to VP16 to be included in the scope of the invention.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

The following examples are provided to illustrate the present invention and are not intended to limit the scope thereof. Those skilled in the art will readily understand that known variations of the conditions and processes of the following preparative procedures can be used to prepare these cell lines.

Cell Lines

Chinese hamster ovary (CHO) cell line (CHO-DUKX-B11) was obtained from L. Chasin (Urlaub et al., *Proc. Natl. Acad. Sci.* vol. 77; pp. 4216–4220, 1980) and cultured in Ham's F12 containing 5% fetal bovine serum (JRH Biosciences) and 2 mM L-glutamine (JRH Biosciences). This formulation is designated CHO growth media.

The BHK-21 cell line was obtained from the A.T.C.C. (Rockville, Md.). BHK-21 cells were normally cultured in Dulbecco's modified Eagle media (DMEM), high glucose (JRH Biosciences, Lenexa, Kans.), supplemented with 2 mM L-glutamine and 10% bovine calf serum (GIBCO-BRL, Grand Island, N.Y.) and 100 units of streptomycin and 100 micrograms (ug) of penicillin per milliliter. This formulation is designated BHK-21 growth media. To isolate BHK/VP16, 10% charcoal-stripped (Danesch et al., EMBO J. vol. 6, pp. 625–630, 1987) fetal bovine serum was used in place of calf serum. BHK-21 cells transfected with pSV2neo (A.T.C.C.) and/or pMON1118 (Highkin et al., *Poultry Science,* vol. 70, pp. 970–981, 1991) were cultured in media supplemented with "GENETICIN"™ (400 ug/ml) and/or hygromycin B (Calbiochem, San Diego, Calif.) (453 units/ml), respectively. These media are designated selective media. "GENETICIN"™ concentrations are given in active strength. pMON1118 (Highkin et al., supra) expresses the hygromycin B resistance gene from the SV40 promoter. A similar plasmid is available A.T.C.C., pSV2-hph. Plasmids that express the dhfr gene, such as SV2-dhfr are also available from A.T.C.C. as is pSV2neo.

Constructs

Restriction enzyme digests and other molecular cloning techniques such as filling in of 5' overhanging restriction fragments ends were according to Maniatis et al., *(Molecular Cloning: A Laboratory Manual,* Cold Spring Harbor Laboratory, 1982). Vectors were treated with calf intestine alkaline phosphatase (Boehringer Mannheim, Indianapolis, Ind.) before ligation using T4 DNA ligase (Boehringer Mannheim or Biolabs, Beverly, Mass.). Restriction fragments were isolated from 1% agarose gels by electroelution onto DEAE cellulose (D-Gel apparatus, Kontes Scientific Glassware/Instruments, Vineland, N.J.).

Figure 1:
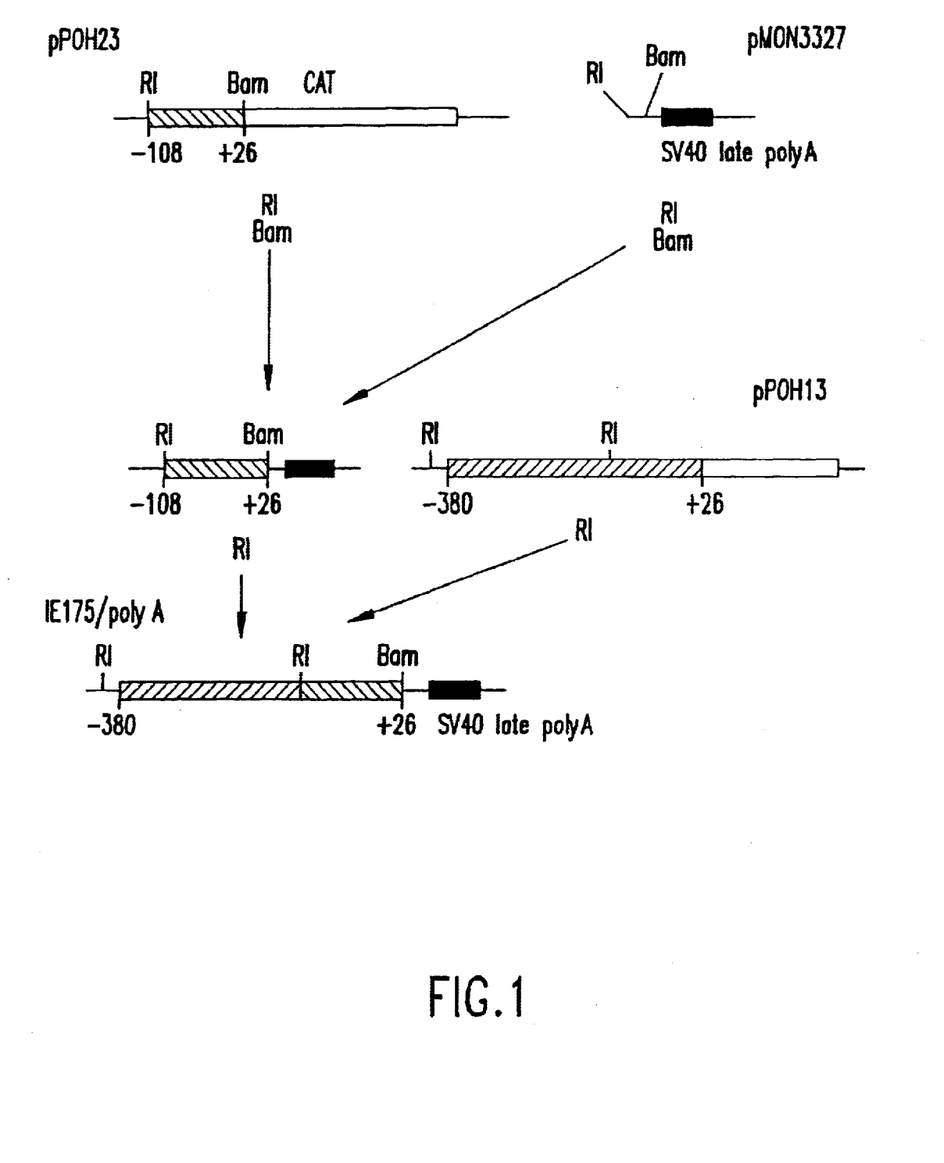
FIG. 1 shows the construction of an IE175 expression vector. This expression plasmid has a unique BamH I site between the promoter sequences and the SV40 late polyadenylation sequences.

An expression vector containing a portion of the IE175 promoter region (−380 to +26) was constructed in several steps (FIG. 1). Plasmid pPOH23 (O'Hare et al., *J. Vir.,* vol. 61, pp. 190–199, 1987) which contains the IE175 promoter region from −108 to +26 (relative to the start of transcription) was digested with EcoRI and BamHI. The 134 base pair fragment that contains the −108 to +26 promoter region was subcloned into the BamHI site of pMON3327 (Highkin et al., supra) which is a pUC18 derivative containing the SV40 polyadenylation signal (nucleotides 2533 to 2770 from the SV40 virus genome). The new plasmid is called −108 to +26 IE 175/polyA. To isolate the remaining sequences of the portion of the HSV IE175 promoter region described above, pPOH13 (O'Hare, supra) which contains the IE175 promoter region from −380 to +26 was digested with EcoRI and the 301 base pair fragment was ligated into −108 to +26 IE 175/polyA at the EcoRI site. The new plasmid has the −380 to +26 region of the IE175 promoter upstream from a unique BamHI site which is followed by a portion of the SV40 late polyadenylation region and is designated IE175polyA.

Figure 2:
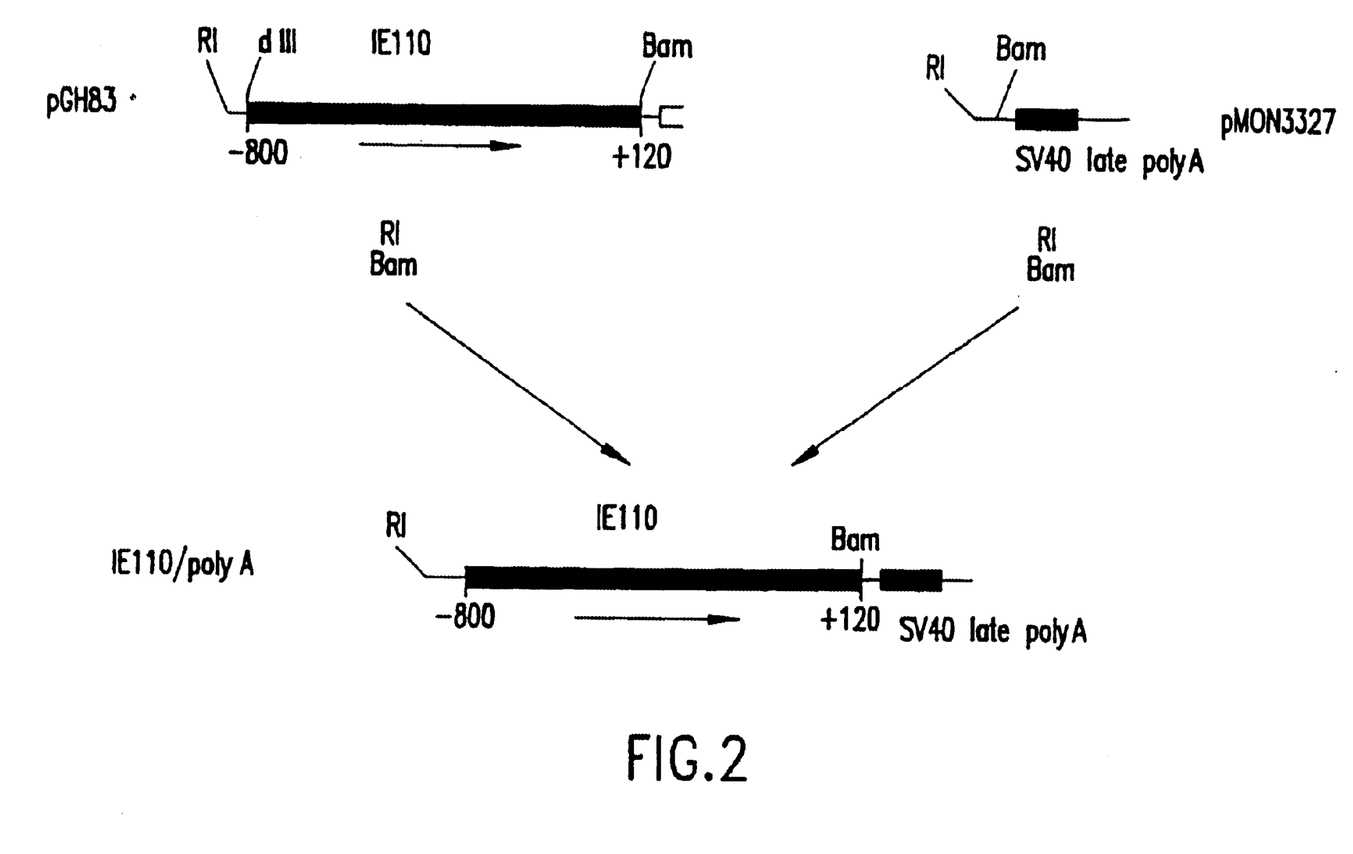
FIG. 2 shows the construction of an IE110 expression vector. This expression plasmid has a unique BamH I site between the promoter sequences and the SV40 late polyadenylation signal.

An expression vector containing the IE110 promoter region was constructed as follows. The HSV IE110 (−800 to +120) promoter region and a small amount of pBR322 sequence was isolated from pGH83 (Roberts et al., *J. Vir.,* vol. 62, pp. 4307–4320, 1988) by digestion with EcoRI and BamHI. The 951 base pair fragment was isolated and ligated to pMON3327 which had been digested with EcoRI and BamHI (FIG. 2). The new plasmid is called IE-110/polyA.

Figure 3:
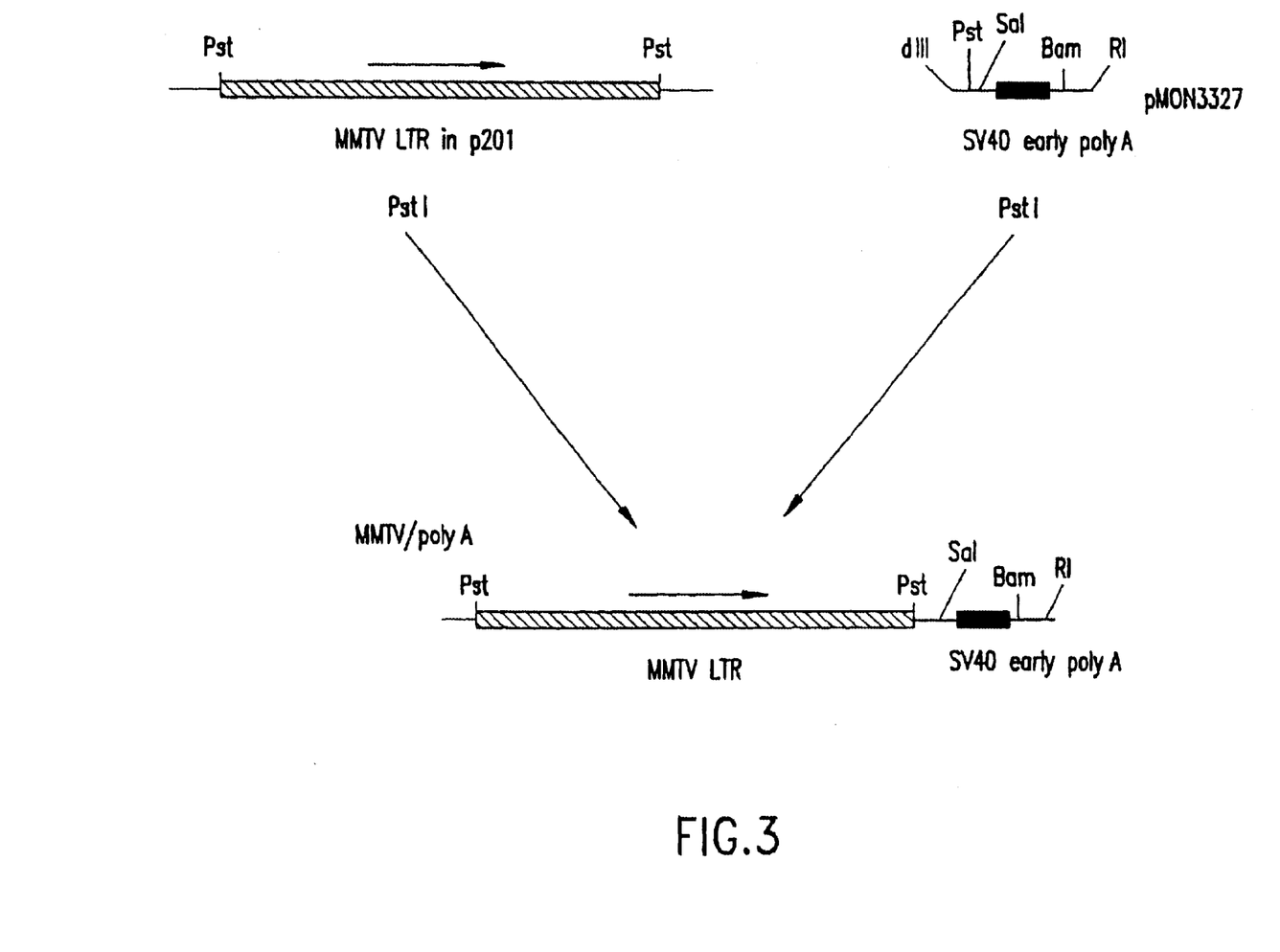
FIG. 3 shows the construction of a mouse mammary tumor virus (MMTV) long terminal repeat (LTR) expression vector. The SV40 polyadenylation signal is in the early orientation in this plasmid.

A vector containing the mouse mammary tumor virus long terminal repeat (MMTV LTR) was constructed by isolating the 1.4 kbp MMTV sequences from p201 (A.T.C.C.) by PstI digestion and ligating into PstI-digested pMON3327. This new vector is designated MMTV/polyA (FIG. 3).

The VP16 coding sequences were isolated from pGH62 (ApRhys et al. *Journal of Virology,* 63, pp. 2797–2812, 1989) by the polymerase chain reaction (PCR) using the manufacturer's procedures using the "GENEAMP"™ (Perkin Elmer Cetus, Norwalk, Conn.) DNA Amplification Reagent Kit and the "AMPLITAQ"™ (Perkin Elmer Cetus) recombinant Taq polymerase. This plasmid contains the 4.7 kilobase pair (Kbp) BamHI F fragment from HSV-1 (strain MP). The sequence of VP16 is in the GenBank database, accession number X03141. The 5' primer has the sequence 5'-GATCGGATCCAACCCCACCCA<u>ATG</u>GAC CTC-3' (SEQ ID NO:1). This primer incorporates a BamHI (GGATCC) site at the 5' end of the PCR product. The initiator methionine is underlined. The 3' antisense primer has the sequence 5'-GATCGGATCCGCGCCCC<u>CTA</u>CCCA CC-3'(SEQ ID NO:2). This primer incorporates a BamHI site at the 3' end of the PCR product. The termination codon is underlined as a point of reference. The VP16 coding region is also available in plasmid pMSVP16 (Novagen, Inc., Madison, Wis.). The PCR product was subcloned into pUC18 which had been digested with BamH I. The VP16 gene in pUC18 was isolated by BamH I digestion and the 5' overhanging ends were filled-in using the Klenow polymerase before ligation into MMTV/polyA which was previously digested with SalI and treated with Klenow polymerase. This VP16 vector is designated MMTV-VP16.

Plasmid pCA21 (obtained from G. Hayward, Johns Hopkins School of Medicine, Baltimore, Md.) has the VP16 coding region under control of the SV40 virus early promoter. A similar plasmid can be constructed by removing the VP16 coding region from pMSVP16 (Novagen, Madison, Wis.) and inserting it into plasmid pSVK3 (Pharmacia LKB Biotechnology, Piscataway, N.J.) by techniques known to the art (Maniatis et al., *Molecular Cloning: A Laboratory Manual,* Cold Spring Harbor Laboratories, 1982) such that the VP16 coding region is under control of the SV40 early promoter.

Western Blot

Cells were washed with phosphate buffered saline (PBS) (available from GIBCO-BRL), harvested by scraping into 1.0 ml PBS and pelleted in a microfuge for 3 minutes. Cells were lysed in 100 microliters of 1.5× sample buffer (3×=7.5 mM Tris-HCl, pH 6.8, 30% glycerol, 4% SDS, 1.5 mM EDTA, 400 microgram/ml bromophenol blue and 60 mM dithiolthreitol), heated at 70° C. for 10 minutes and boiled for 3 minutes. The debris was pelleted before loading 10 to 20 microliters of the supernatant on 10% SDS-PAGE minigels (Daiichi, Integrated Separation Systems, Hyde Park, Mass.). After electrophoresis, the proteins were transferred to immobilon-P (Integrated Separation Systems) using a semi dry blotter (Janssen, JKA-Biotech, Denmark). Following transfer, the remaining unbound binding sites of the membrane were bound by incubation with blocking solution (0.25% geletin, 100 mM Tris-HCl, pH 9.0) overnight at room temperature. The blocking solution was removed and the membrane was incubated in NET buffer (150 mM NaCl, 5 mM EDTA, 50 mM Tris-HCl, pH 7.5) plus 0.25% gelatin and 0.05% NP40 containing rabbit antisera (1:2000 dilution) raised against a carboxyl terminus peptide of VP16 (amino acids 477–490) at 37° C. for 2 hours. The membrane was washed with NET/gelatin/NP40 buffer minus the antisera at room temperature for 1 hour and incubated with NET/gelatin/NP40 buffer containing 0.3 mCi/ml $^{125}$I-Protein A (Amersham, Arlington Heights, Ill., 0.1 mCi/microliter) for 1 hour at room temperature. The isotope was removed by washing in high salt NET (1 M NaCl) containing 0.4% sarkosyl. After rinsing with water and air drying, the blots were exposed to X ray film "KODAK, X-OMAT AR™" using an intensifying screen "DUPONT LIGHTNING PLUS™".

Stable Transfection Conditions

Cells were seeded in 60 mm tissue culture dishes at 2 to 3×10$^5$ cells per dish, 24 hours before transfection. Cells were transfected either by the CaPO$_4$ procedure (van der Eb et al.,

*Methods in Enzymology,* vol. 65, Grossman and Moldave, eds. Academic Press, NY, 1980) followed by glycerol shock four hours after transfection (Frost et al., *Virology,* vol. 91, pp. 539–560, 1978) or by using the "LIPOFECTIN"™ reagent (GIBCO-BRL) according to the manufacturer's recommendations and using 40 ug of "LIPOFECTIN"™ reagent in 3.0 ml of "OPTIMEM"™/beta-mercaptoethanol (GIBCO-BRL) per 60 mm dish of cells. The transfection media was aspirated after 6 hours and replaced with growth media. The cells were transferred, after 2 days, into 5 to 10 100 mm dishes and fed selective media. Antibiotic resistant colonies were isolated 2 to 3 weeks later and transferred to 24 well tissue cluster plates. When the wells were 50 to 100% confluent, supernatant was screened for the product of the gene of interest. Positive lines were expanded and designated as producer lines.

Standard Assay for Determining tPA and bGH Production

Producer lines were seeded into two wells of a 6 well tissue cluster dish at 2.5 to $5.0 \times 10^5$ cells per well and fed 3 ml of growth media (without the presence of selectable agents). The next day the media was replaced with 3 ml of fresh media and 24 hours later, duplicate aliquots of supernatant were harvested and stored at −20° C. until assayed. The final cell count was determined and protein production was normalized for micrograms protein produced per 24 hours per $1 \times 10^6$ cells.

EXAMPLE 1

Generation of Stable Cell Lines that Express VP16 in BHK-21 Cells and Subsequent Expression of tPA and bGH BHK-21 cells that were cotransfected with MMTV-VP16 (20 ug) and pSV2neo (2 ug) were selected for "GENETICIN"™ resistance and 34 cell lines were isolated. The lines were first screened by Western blot using rabbit antisera raised against the carboxy terminus peptide of VP16 (amino acids 477–490). One line, #2, had a faint band in the Western blot that comigrated with VP16 (data not shown). Line #2, along with 5 other putative positive lines, was further tested by transient transfection with 5 ug of IE175-CAT (pPOH13). A similar plasmid, pICP4CAT, is available from Novagen Inc. (Madison, Wis.). The day after transfection, the growth media was changed to media supplemented with 1 uM dexamethasone (Sigma, St. Louis, Mo.). The following day, the cells were harvested and assayed for CAT activity (Neumann et al., *BioTechniques,* vol. 5, pp. 444–447, 1987). To identify a VP16 expressor cell line, CAT activity in the putative positive lines was compared to CAT activity seen in the BHK-21 parental. Line #2 had a 12-fold increase in CAT activity when compared to the BHK-21 parental control and was named BHK VP16 (data not shown). Although Western blotting was the method of isolation of the BHK/VP16 line, a preferred method might be a functional assay using an IE175-beta-galactosidase (B-gal) construct. The *E. coli* B-gal gene (GenBank accession number V00296) was isolated as a BamHI fragment (approximately 3.3 Kbp) from a plasmid which contains the gene under control of the rat prolactin promoter. Similar B-gal cassettes are available commercially (Promega, Madison, Wis.; Pharmacia-LKB, Pistaway, N.J.). The BamHI fragment was subcloned into IE175/polyA to form IE175-B-gal. Cell lines were screened for VP16 activity as follows. Cells were seeded at approximately $1 \times 10^4$ cells per well of a 48-well tissue cluster dish and were transfected with IE175-B-gal using "LIPOFECTIN"™ reagent.

Approximately 40 hours later, the cells were lysed in situ by the addition of 0.5% NP40 in Hank's buffered saline solution (GIBCO-BRL,) containing 0-nitrophenyl-beta-D-galactopyranoside (ONPG, Sigma) according to Lim et al. (*BioTechniques* vol. 7, pp 576–579, 1989). After 60 minutes, a 200 microliter sample was transferred to a well of a 96-well tissue cluster plate. The 96-well plate was centrifuged (Beckman JS 5.2 rotor, 500×g, 10 minutes) and 100 microliters were transferred to each well of a new 96-well tissue cluster plate. The optical density at 410 nmeters was determined using a plate reader (Dynatech, MR600). The amount of protein was determined by assaying 20 microliters of the lysate in 200 microliters of the BCA (Pierce, Rockford, Ill.) protein reagent.

The human tissue plasminogen activator (tPA) cDNA was modified by site directed mutagenesis to truncate the 5' and 3' noncoding regions and to place unique BamHI sites at the ends. The modified cDNA contains 19 base pairs of 5' untranslated sequence and terminates 4 base pairs after the termination codon resulting in a 1.7 kbp fragment. This fragment was digested with BamHI and ligated into the BamHI site of IE175/polyA to form plasmid IE175-tPA and into the BamH I site of IE-110/polyA to form plasmid IE110-tPA.

The BHK/VP16 cell line was used to engineer three sets of high protein producing cell lines. The first set was made by cotransfecng BHK/VP16 with the IE175-tPA (20 ug) and pMON1118 (2 ug) plasmids. Fifty-five cells lines, resistant to "GENETICIN"™ and hygromycin B were isolated and screened for tPA production and 41 were positive.

Tissue plasminogen activator (tPA) was assayed in the conditioned media of transfected cell lines by the particle concentration fluorescence immunoassay (PFCIA) (Jolly et al., *Journal of Immunological Methods,* 67, pp. 21–35, 1985). Epicon assay plates, Particle Concentration Analyzer (PCA) and polystyrene particles were purchased from IDEXX Laboratories, Inc. (Westbrook, Me.). Purified human tPA and goat antihuman tPA antibodies were obtained from American Diagnostica Inc. (Greenwich, Conn.). Reagents were prepared according to the suppliers protocols and the basic PFCIA was established according to the manufacture's protocols. Briefly, polystyrene particles were coated with the goat anti-tPA antibodies to capture tPA in the conditioned media. The conditioned media samples were incubated with the goat anti-tPA polystyrene particles and with fluorescein-labeled goat anti-tPA antibodies. After 30 minutes, a complex was formed on the polystyrene particles. The complex was washed and the amount of fluoresence was quantitated by the PCA. Antibodies were labeled with fluorescein using fluorescein isothiocyanate (Sigma, St. Louis, Mo.). An alternative approach is to purchase an enzyme-linked-immunosorbent-assay (ELISA) kit for tPA from American Diagnostica.

The 16 highest producer cell lines from the initial screening were assayed for tPA production under standard conditions. Nine lines were positive with 5 lines producing concentrations of tPA in excess of 1 ug/$10^6$ cells/24 hours (Table 1). As a control, BHK-21 cells which do not express VP16 and were cotransfected with IE175-tPA and pMON1118 were screened for tPA production. Of 64-hygromycin resistant lines, 41 were positive for tPA production in the initial screen. Fifteen lines were reassayed under standard conditions and 6 were positive for tPA. The levels of tPA production ranged from 0.007 ug to 0.176 ug/$10^6$ cells/4 hours (Table 1).

To determine whether the high level protein production was limited to the IE175 promoter only, a second set of cell lines were engineered by cotransfecting the transactivator line, BHK/VP16, with IE110-tPA and pMON1118. Fourteen of the 19 "GENETICIN"™/hygromycin lines isolated were positive for tPA production. Of these 14 lines, 3 lines produced high levels of tPA with levels ranging from 4 to 21 ug/$10^6$ cells/24 hours (Table 1). To determine the levels of tPA production in the absence of VP16 transactivator, BHK-21 parental cells were transfected with IE110-tPA and pMON1118. Eighteen hygromycin resistant lines were screened for tPA production. The three highest producer lines made 0.014 to 0.08 ug tPA/$10^6$ cells/24 hour (Table 1). This experiment demonstrates that the stable high level of expression of tPA from the BHK-21 cells in the presence of VP16 expression is not limited to the transactivation of the IE175 promoter but, also extends to other HSV IE promoters.

In order to show that the high level of protein production was not a function of the tPA molecule itself, a third set of experiments was done using the bovine growth hormone (bGH) gene.

The genomic bGH gene (GenBank accession number J00008) was obtained from pBR-bGH (Ramabhadran et al., *Gene* 38, pp. 111–118, 1985) by PCR. The 5' primer anneals about 60 base pairs upstream of the initiator codon and has the sequence 5'-GACCAATTCCAGGATCCCAGGACCC AGT-3' (SEQ ID NO:3) and contains a natural BamHI site. The 3' antisense primer ends about 20 base pairs downstream of the termination codon and contains an engineered B a m H1 site. This primer has the sequence 5'GATCGG TACCGCAAACAACAGATGGCTGGCAACTAGA-3' (SEQ ID NO:4). The PCR product (approximately 1.7 kbp) was digested with BamH and inserted into the BamHI site of plasmid IE175/polyA to form IE175-bGH.

The transactivator line, BHK/VP16 was cotransfected with IE175/bGH (20 ug) and pMON1118 (2 ug). Forty-two "GENETICIN"™/hygromycin resistant lines were screened for bGH production. Forty of these lines were positive for bGH in the conditioned media. The assay for detection of bGH was a PCFIA as was the tPA assay (see above). In this case, two different affinity-purified monoclonal antibodies were used. One antibody was used to coat the beads and the other was labeled with fluorescein and used to detect the captured bGH on the beads. Biologically active bGH was purified from *E. coli* and used as the standard. Standard assays of 15 positive lines showed that they were producing 3 to 19 ug bGH/$10^6$ cells/24 hours (Table 1). As a control, BHK-21 parental cells were cotransfected with IE175-bGH and pMON1118. Fifty-three hygromycin resistant lines were screened for bGH production and 50 were positive. Standard assays of 19 of the highest producer lines identified in the screen showed that they produced from 0.33 to 5 ug bGH/ $10^6$ cells/24 hours. This result was surprising since the values predicted from the experiments with IE175-tPA and IE110-tPA were <0.3 ug tPA/$10^6$ cells/24 hours. However, the amount of bGH produced from the VP16 transactivator line was several fold more, on average, than from the parental BHK-21 line. However, bGH may not be a representative marker protein because there seems to be a high level of constitutive production in other systems in the absence of induction (G. Hayward, personal communication).

Therefore, the VP16 transactivator-coupled mammalian expression system can be used for the efficient isolation of cell lines that produce large quantities of protein by utilizing the IE110 or the IE175 promoters. This implies that the promoter regions of the other immediate early genes of HSV-1 or HSV-2 are also good targets for transactivation-coupled vector design.

Stability of Expression

Figure 4:
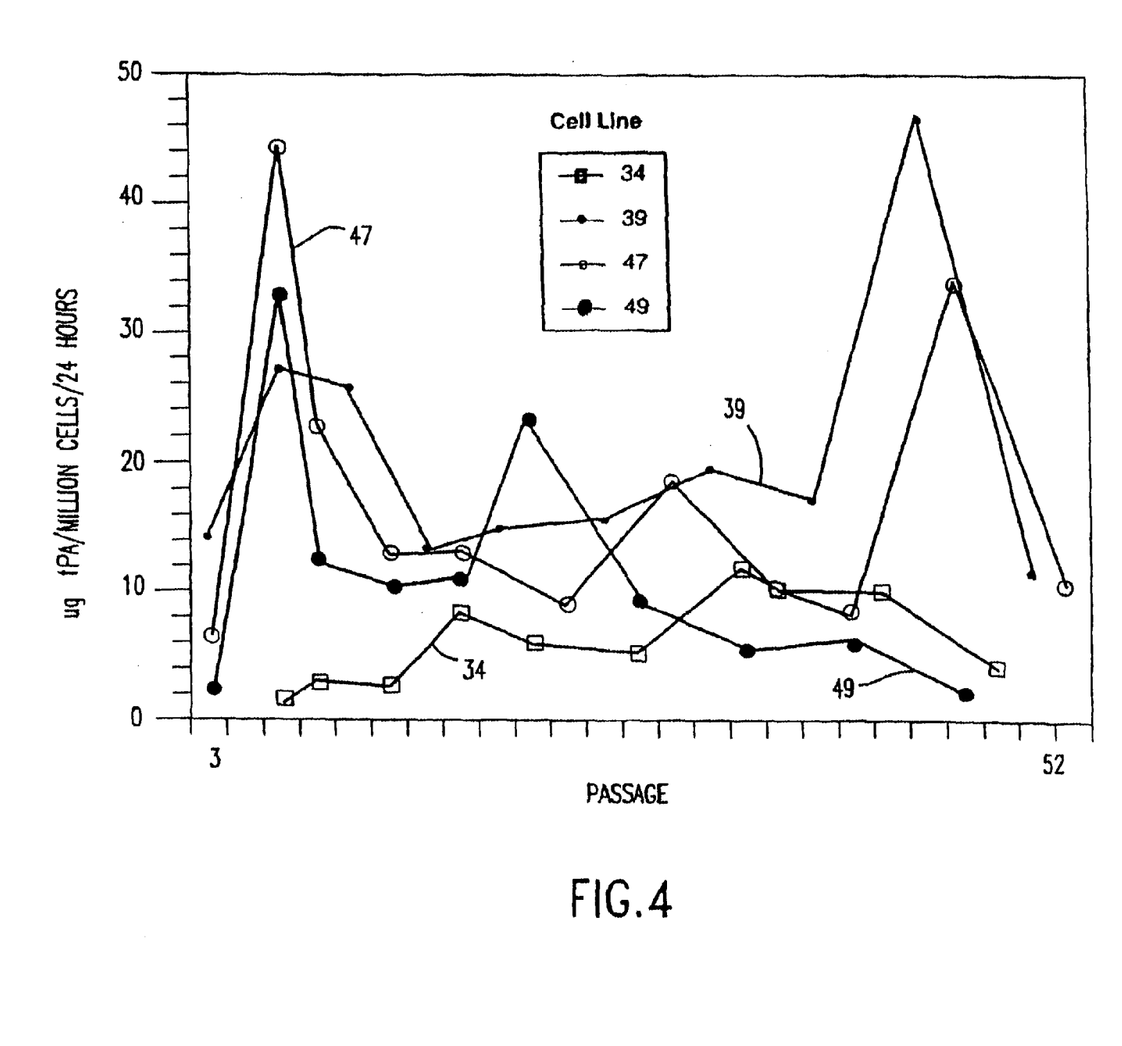
FIG. 4 BHK/VP16/IE175-tPA lines 34, 39, 47 and 49 were passaged at 1:20 to 1:40 (by volume) twice per week and assayed for production of tPA.

The cell lines that have been in continuous culture the longest are the ones generated by cotransfection of IE175-tPA and pMON1118 into the BHK/VP16 line (FIG. 4). The initial standard assay at passage three showed expression levels of less than 10 ug tPA/$10^6$ cells/24 hours for all four lines. By passage 6, a startling increase in tPA production was seen in three of the lines with levels ranging from 27 to 44 ug/$10^6$/24 hours. tPA levels after passage 6 declined for these three lines, and seemed to be stabilizing at around 10 to 15 ug/$10^6$/24 hours. For a fourth line, #34, which did not show a large increase in tPA production at passage 6, the levels appear to be more consistent over time. The level of tPA production remained in the 5 to 20 ug/$10^6$ cells/24 hour range as measured by PFCIA over approximately 52 passages. Each passage represents 3 to 5 population doublings per week. tPA levels have been verified by the amidolytic assay (T. C. Wun, data not shown) as described below. Aliquots of the tPA conditioned media were diluted into 1 M $NH_4HCO_3$ plus 1 mg/ml BSA. To 20 microliters of the diluted tPA sample in a disposable cuvette was added 0.225 ml of 0.1 M Tris/HCl, pH 8.7, plus 0.5% Triton X-100. The mixture was incubated at 37° for 3 minutes. Five microliters of conditioned media was added and the absorbance change at 405 nm was measured in a Gilford spectrophotometer. Single-chain tPA activity standard (American Diagnostica product #115) dissolved in 1M $NH_4HCO_3$ plus 1 mg/ml BSA was used as reference.

EXAMPLE 2

Vascular Permeability Factor (VPF)

Complementary DNA (cDNA) containing the VPF coding region was initially isolated from a phorbol ester-induced U937 cell library as described (Keck et al. *Science* 246, pp. 1309–1312, 1989). The cDNA encodes a protein of 189 amino acids and is designated VPF189 [EMBL/ GenBank accession number X15997 or M27281]. Using PCR technology two other forms of VPF cDNA were isolated. One form encodes a 165 amino acid protein that is identical to VPF189 except that amino acids 116 to 138 are deleted due to alternate splicing and is designated VPF165. Another form encodes a protein of 121 amino acids and is identical to VPF189 except that amino acids 116 to 158 have been deleted due to alternate splicing and is designated VPF121.

All of the above cDNAs of VPF (VPF189, VPF165, and VPF121) were subconed into the BamHI site of IE175/ polyA. In addition, the three cDNAs of VPF were subcloned into a bovine papillomavirus (BPV) vector, pMON1123, under the control of the mouse metallothionein promoter (Keck et al. supra). Lastly, the three cDNAs of VPF were subcloned under the control of the Rous sarcoma virus long terminal repeat (RSV LTR) promoter in a plasmid that also contains a SV2-dhfr expression cassette. The IE175/polyA derived VPF expression plasmids were cotransfected with pMON1118 into the BHK/VP16 transactivator line, as described above. The BPV derived VPF expression plasmids were cotransfected into mouse C127 cells (A.T.C.C.) with SV2neo and selected for "GENETICIN"™ resistance. The RSV LTR/SV2-dhfr derived VPF expression plasmids were transfected into CHO-DUKX-B11 cells and selected for expression of DHFR (Kaufman, *Methods in Enzymology*, vol. 185, D. V. Goeddel, ed., Academic Press, New York, pp. 537–566, 1990). Cell lines from each of the above sets of transfections were isolated using the appropriate selection method and conditioned media from the lines was tested for the presence of VPF, originally using the Miles assay (Connolly et al., *Journal of Biological Chemistry* vol. 264, pp. 20017–20024, 1989) but preferably by enzyme linked immunosorbant assay (ELISA) (Harlow et al., supra) as follows.

Goat anti-VPF IgG was bound to a polyvinyl chloride microtiter plate by incubating each well with 50 microliters of a 20 ug/ml solution of the antibody diluted in PBS for 2 to 3 hours at room temperature. The antibody solution was removed and the wells were incubated for 30 minutes at room temperature with 1% fat free dry milk (casein) diluted in PBS to block any remaining unbound sites. The wells were washed four times with 0.15 M NaCl containing 0.05% Tween 20 (Sigma). Conditioned media was added to the wells and incubated overnight at room temperature. The wells were washed four times with the NaCl/Tween 20 solution. 50 microliter of 2.5 ug/ml biotinylated goat anti-VPF IgG was added and incubated for 2 to 3 hours at room temperature. The wells were washed four times and a 50 microliter aliquot of 1/1600 dilution of a horseradish peroxidase-strepavidin (KPL, Gaithersburg, Md.) solution was added for 90 minutes at room temperature. The wells were washed and 100 microliters of horse radish peroxidase substrate was added and assayed as per the manufacturer's instructions. Concentrations of VPF were determined from a standard curve using U937 cell-derived VPF diluted in PBS containing 0.05% Tween 20 and 1% fat-free dry milk. Table 2 shows that the BHK/VP16 line was as efficient at producing the three forms of VPF as the C127 cells, a line in which the BPV vector is typically amplified from 10 to 200 copies per cell.(Stephens et al., *Biochemical Journal* 248, pp. 1–11, 1987) and much more efficient than the CHO-DUKX-B11 system before amplification. Moreover, BHK-21 cells do not have the disadvantages that the C127 cells have during scale up (McKillip et al., *Bio/Technology* 9, pp. 805–810, 1991). The production of VPF189 was low (<0.1 ug/ml)in all cell systems tested due to degradation of the protein in the media (data not shown). Levels of VPF 189 mRNA in the cells was just as high as the levels of VPF165 and VPF121 in the respective cell lines (data not shown) indicating that the level of transactivation is not responsible for the apparent decreased production of VPF189 protein.

EXAMPLE 3
Human Intercellular Adhesion Molecule (ICAM)

A cDNA (GenBank accession number J03132) encoding the amino-terminal extracellular domain, the transmembrane domain and the carboxy-terminal intracellular domain of ICAM was isolated by PCR as follows. SK-Hepatoma cell (A.T.C.C.) RNA was used as the template for specifically primed first-strand synthesis using a 3' antisense primer 5'-GCTAGGATCCCGGGATAGGTTCAGGGAGGCG-3' (SEQ ID NO:5) which is complementary to nucleotides 1646 to 1669 of the ICAM cDNA The 20 microliter reaction contained 10 ug of RNA, 20 picomoles of primer, 20 units of "RNASIN"™(Promega, Madison, Wis.), 2.5 mM dNTPs and 200 units of reverse transcriptase. The synthesis was carried out at 37° C. for 30 minutes and then immediately used for amplification using PCR as per the manufacture's directions. The 5' primer has the sequence 5'-GATC GGATCCTCAGCCTCGCTATGGCTCCC-3'(SEQ ID NO:6) and is complementary to nucleotides 45 to 66 of the ICAM cDNA (Staunton et al., *Cell,* 52, pp 925–933, 1988). In addition, the primer includes an engineered BamHI (GGATCC) restriction site. The resulting fragment of about 1.6 kbp was used as a template for a subsequent PCR reaction using the same 5' primer and a new 3' antisense primer such that the 3' primer led to truncation of the molecule at amino acid 453 thereby excluding the transmembrane and cytoplasmic domains of the molecule (Marlin et al., *Nature* 344, pp. 70–72, 1990). Sequence of the second 3' antisense primer was 5'-GATCGATCATGGATCC CTCATACCGGGGGGAGAG-3'(SEQ ID NO:7) and is complementary to nucleotides 1480 to 1497 of the ICAM cDNA and introduces a BamHI site immediately 3' to the glutamic acid codon (amino acid 435). Plasmid IE175/polyA was modified by digestion with BamHI and ligated to a DNA fragment containing a BamHI site at the 5' end, a sequence encoding a decapeptide (YPTDVPDYAS) (Huse et al. *Science,* 246, pp. 1275–1281, 1989, single letter code), a termination codon and a BglII site at the 3' end. This fragment was generated by annealing two oligonucleotides, 5'-GATCCTACCCGTACGACGTTCCGGACTACGCTT CTTAAGAGCTC-3'(SEQ ID NO:8) and 5'-GATCGAG CTCTTAAGAAGCGTAGTCCGGAACGTCGTACGGG TAG-3'(SEQ ID NO:9). This modified IE175/polyA plasmid was designated IE175/deca-polyA and was digested with BamHI and ligated to the truncated ICAM cDNA fragment which had also been digested with BamHI resulting in plasmid IE175-sICAM$_{453}$-deca-polyA. The sICAM$_{453}$ expression vector, was cotransfected into the BHK/VP16 line with pMON1118 as described and high level producers of sICAM$_{453}$-decapeptide were selected. The "GENETICIN"™/hygromycin B resistant cell lines were screened for expression of sICAM$_{453}$-decapeptide by screening for the decapeptide portion of the fusion protein by immunoblot analysis. Upon reaching confluency, cells were incubated in serum free DMEM for 24 hours. A 100 microliter aliquot of conditioned media was harvested and filtered onto nitrocellulose filter paper using a multichamber slot blot apparatus (Schleicher and Schuell). The nitrocellulose was then probed with rabbit polyclonal antisera raised against the decapeptide (Huse et al supra.) as follows. The nitrocellulose was incubated for 1 hour at 37° C. in a 5% solution of bovine serum albumin (BSA) in TNT buffer (150 mM NaCl, 10 mM Tris-HCl, pH 8.0, 0.05% Tween 20) to block nonspecific antibody binding sites. Following washing with TNT buffer, the nitrocellulose paper was incubated with the rabbit anti-decapeptide antibody at a 1:4000 dilution in 1% BSA/TNT for 1.5 hours at room temperature. The unbound antibody was removed by three 20 minute washes of paper in TNT buffer. The rabbit antibody was detected using a goat anti-IgG alkaline phosphatase detection system such as that available from Promega (Madison, Wis.) as per manufacturer's instructions. sICAM$_{453}$-decapeptide in the conditioned media was quantitated by displacement of $^{125}$I-labeled sICAM$_{453}$-decapeptide from plates bound with a polyclonal antisera to the decapeptide. Rabbit anti-decapeptide IgG was purified on an "Affi-Gel 15"® (Registered trademark of BioRed) resin (BioRed, Richmond, Calif.) to which the decapeptide was coupled. Wells of a 96-well microtiter plate are bound with the anti-decapeptide IgG, nonspecific binding sites are blocked with BSA and then the wells are incubated with 25 microliters of conditioned media from the producer lines and 25 microliters (50,000 cpm) of $^{125}$I-labeled sICAM$_{453}$-decapeptide. After washing, the amount of radioactivity bound by the wells is determined and compared to the amount of radioactivity left bound after competition by a known amount of unlabeled sICAM$_{453}$-decapeptide. Table 2 shows that the highest producer synthesized 100 micrograms of secreted ICAM per milliliter, comparable to expression levels achieved by hybridomas (Bendig, *Genetic Engineering,* vol. 7, pp. 90–127, 1988).

EXAMPLE 4
Secreted Fucosyltransferase

The expression vector for a secreted form of fucosyltransferase (accession number X53578, Kukowska-Latallo et al., *Genes and Development* 4, pp. 1288–1303, 1990) was made in several steps. Plasmid IE110/polyA (FIG. 2) was digested with BamHI. Into the BamHI site was cloned a fragment of doublestranded DNA which encodes the human IL3 signal sequence (underlined) with engineered complimentary BamHI ends 5'-GATCCACC<u>ATGAGCCGCCGTCCCGT CCTGCTCCTGCTCCAACTCCTGGTCGGCCCCGCCA TGGCT</u> AAGCTTGGATC-3'(SEQ ID NO:10) and includes engineered NcoI (CCATGG) and engineered HindIII (AAGCTT) sites toward the 3' end of the signal peptide coding sequence. The resulting plasmid (IE110-IL3/polyA) was digested with NcoI and HindIII. Into this site was ligated a fragment of DNA that codes for a decapeptide [YPYDVPDYAS, single letter code, (SEQ ID NO:11] with a NcoI site at the 5' end and a HindIII site at the 3' end. This fragment was derived by annealing the oligonucleotide 5'-GATCGACCATGGCTGCCATACCCGTACGACGTT CCGGACTACGCTTCTAAGCTT-3'(SEQ ID NO:12) with its complementary oligonucleotide. The resulting plasmid is designated IE110-IL3-deca/polyA. A DNA fragment that codes for part of the fucosyltransferase gene was isolated from A431 (A.T.C.C.) cell RNA by PCR and has engineered HindIII ends. The fucosyltransferase coding sequence of the fragment begins with amino acid 44 (serine) and ends 4 bp after the natural termination coding. This fragment was ligated into the HindIII site located behind the decapeptide sequence in IE110-IL3-deca/polyA. The resulting fusion gene has the human IL3 signal sequence (first 19 amino acids), a synthetic decapeptide coding region and the fucosyltransferase coding region beginning with amino acid 44 and is designated IE110-IL3-deca-FT-polyA.

BHK/VP16 cells were cotransfected with IE110-IL3-deca-FT-polyA and pMON1118 as described above. Cell lines were assayed for secreted fucosyltransferase activity according to Prieels et al. (*Journal of Biological Chemistry*, 256, pp. 10456–10463, 1981). When converted into ug/ml, the highest producer line made 70 micrograms per milliliter (Table 2).

EXAMPLE 5

This example demonstrates the construction of CHO cell lines which are high level producers of tPA This example shows that selection for dihydrofolate reductase (DHFR) expression in the presence of herpesvirus VP16 leads to a smaller number of higher level tPA producers in CHO DUKX-B11 cells. Selection for an antibiotic resistance marker leads to a higher percentage of high level producers in CHO DUKX-B11 cells.

The cells were cotransfected with either pCA21 or MMTV-VP16 and pSV2neo. Transfectants were selected which were resistant to "GENETICIN"™ and were screened for VP16 expression by transfection with IE175-B-gal as described above.

Cells which expressed VP16 were cotransfected with either IE175-tPA or IE110-tPA; and pMON1118 or pSV2dhfr. The results are shown in Table 3.

The data shows that only 3/127 CHO/VP16/175-tPA cell lines which were selected for DHFR expression expressed high levels of tPA (i.e., over 1.0 ug/$10^6$ cells/24 hrs.) In contrast, when hygromycin was used as a selective agent 6 percent of cell lines expressed greater than 1.0 ug/$10^6$ cells/24 hrs of tPA.

The control transfections into parental CHO-DUKX-B11 which do not express VP16 are slightly anomolous. Using hygromycin selection, 0/87 cell lines were higher producers as might be expected. However, with DHFR selection, in the absence of VP16, 7/112 cell lines were higher level producers. This high proportion of higher level producers may reflect some level of amplification of the DHFR and tPA genes in the absence of methotrexate. However, we have no data to support this concept.

Further Applications

The cell lines described above express VP16 and produce significant amounts of secreted proteins from genes operably linked to an HSV IE promoter, a transactivating target of VP16. These secreted proteins are readily quantitated ant it is therefore envisioned that these cell lines may be useful in the discovery of compounds that inhibit the VP16-mediated transactivation event. Specifically, natural products, chemicals or other substances may be added to the above described cell lines and the effect on the amount of protein product produced can be determined. Those chemicals, natural products or other substances that decrease the production of the protein product are leads for the identification of compounds that interfere with VP16-induced transactivation. Control cell cultures that secrete proteins under control of other promoters would also be tested with the same compounds to determine whether the decrease in protein production was specific to the VP16 lines. Compounds that specifically decrease the production of protein in the VP16 line would be analysed futher and tested for antiviral activity. The same approach can be used with transient assays. However, transient assays would be much more laborious since they would require DNA transfection for each assay. Since the cell lines described above stably produce the protein products, a much more homogenous supply of cells can be used in many assays. This leads to a saving of time and leads to better reproducibility from assay to assay. Such a practice using stable cell lines was recently used to discover compounds that may inhibit the transactivation of the HIV LTR by the tat transactivator (Hsu et al., *Science*, 254, pp. 1799–1802, 1991). A similar approach is described in application WO 91/01379 (international application number PCT/US90/04021).

It is anticipated that the BHK/VP16 and the CHO/VP16 lines will be useful in the production of mutants of HSV that lack a functional VP16 gene. As shown by Werstuck et al. (*Journal of Virology*, 64, pp. 984–991, 1990) a cell line that expresses VP16 will enhance the infectivity of HSV DNA. Because VP16-minus mutants of HSV and naked HSV DNA lack the ability to transactivate the immediate early events of HSV replication, supplying VP16 in trans by the host cell line will allow efficient replication of the VP16 minus mutants of HSV and enhance the infectivity of the naked HSV DNA. The usefulness of such a VP16 expressing cell line would be in the passage of potential live vaccine forms of HSV which have been rendered noninfectious due to mutations of the VP16 gene. It is anticipated that the VP16 expressing lines may also be engineered with other HSV genes that will complement additional HSV mutants in trans in order to provide the full array of necessary genes for the defective HSV virus.

From the foregoing description, one skilled in the art can easily ascertain the essential characteristics of this invention, and without departing from the spirit and scope thereof, can make various changes and modifications of the invention to adapt it to various usages and conditions. Accordingly the scope of the invention is not to be considered limited to the particular embodiments shown or suggested, but is rather to be determined by reference to the appended claims.

TABLE 1

Production of tPA and bGH in BHK Lines

| Line and Plasmid | Frequency* | Range** |
| --- | --- | --- |
| BHK/VP16, IE175-tPA | 9%(5/55) | 3–15 |
| BHK, IE175-tPA | 0%(0/64) | 0.092–0.176 |
| BHK/VP16, IE110-tPA | 16%(3/19) | 4–21 |
| BHK, IE110-tPA | 0%(0/18) | 0.014–0.08 |
| BHK/VP16, IE175-bGH | 100%(15/ 5) | 8–19 |
| BHK, IE1 75-bGH | 100%(18/18) | 3–5 |

*number of colonies producing over 1 ug/million cells/24hrs
**ug/million cells/24 hrs of top 3 producer lines

TABLE 2

PRODUCTION OF PROTEINS BY VARIOUS EXPRESSION SYSTEMS

| PROTEIN | BHK/VP16 | C127/BPV | BASAL dhfr/CHO |
| --- | --- | --- | --- |
| tPA | 15–20 ug/ml | 15 ug/ml | 0.2 ug/ml |
| VPF121 | 7 ug/ml | 2 ug/ml | 0.05 ug/ml |
| VPF165 | 3 ug/m/ | 3 ug/ml | 0.06 ug/ml |
| VPF189 | 0.03 ug/ml | 0.07 ug/ml | 0.01 ug/ml |
| ICAM** | 100 ug/ml | NT* | NT |
| FT*** | 70 ug/ml | NT | NT |

*NT, Not tested
**secreted ICAM-decapeptide
***secreted fucosyltransferase-decapeptide

TABLE 3

Expression of tPA in CHO Cells

| CELL LINES AND PLASMIDS | Screened | % ug Producer |
| --- | --- | --- |
| CHO/VP16 + IE175-tPA/DHFR* | 127 | 2.4 |
| CHO/VP16 + IE175-tPA/HYGRO | 48 | 6.25 |
| CHO/VP16 + IE110-tPA/DHFR | 41 | 0 |
| CHO/VP16 + IE110-tPA/HYGRO | 37 | 2.7 |
| CHO + IE175-tPA/DHFR | 112 | 6.25 |
| CHO + IE175-tPA/HYGRO | 87 | 0 |
| CHO + IE110-tPA/DHFR | 79 | 0 |
| CHO + IE110 tPA/HYGRO | 60 | 0 |

*Resuts pooled from SV40/VP16 and MMTV/VP16 lines.

---

What is claimed:

1. A method of producing a mammalian cell line for stable expression of a gene product, comprising the steps of:
   cotransfecting a mammalian cell with a first construct which cause said cell to express herpes simplex virus transactivating protein VP16 and a second construct comprising a selectable resistance gene to a first antibiotic;
   selecting said cell which is resistant to the first antibiotic;
   screening said cell which is resistant to the first antibiotic for VP16 expression;
   cotransfecting said cell which expresses herpes simplex virus transactivating protein VP16 with third and fourth constructs, the third construct comprising a herpes simplex virus gene promoter that responds to VP16 operably linked to a gene of interest, and the fourth construct comprising a selectable resistance gene to a second antibiotic;

selecting said cell which is resistant to the second antibiotic;

screening said cell which is resistant to the second antibiotic for expression of the gene product of said gene of interest; and culturing said cell into a stable cell line.

2. The method of claim 1 wherein said mammalian cell is a BHK-21 cell or a dhfr-minus mutant of CHO.

3. The method of claim 1 wherein said herpes simplex virus gene promoter is the IE175 promoter region −380 to +26 or the IE110 promoter region −800 to +120.

4. The method of claim 1 wherein the selectable resistance gene is selected from the group consisting of genes encoding hygromycin phosphotransferase, aminoglycoside phosphotransferase 3' (II), puromycin acetyl transferase and bleomycin-phleomycin binding protein.

5. The method of claim 1 wherein said gene of interest codes for a secreted protein.

6. The method of claim 1 wherein said gene of interest codes for tPA, secreted ICAM, secreted fucosyltransferase, or secreted vascular permeability factor.

7. A stable mammalian cell line which expresses a gene product, said cell line made by the process of:

cotransfecting a mammalian cell with a first construct which cause said cell to express herpes simplex virus transactivating protein VP16 and a second construct comprising a selectable resistance gene to a first antibiotic;

selecting said cell which is resistant to the first antibiotic;

screening said cell which is resistant to the first antibiotic for VP16 expression;

cotransfecting said cell which expresses herpes simplex virus transactivating protein VP16 with third and fourth constructs, the third construct comprising a herpes simplex virus gene promoter that responds to VP16 operably linked to a gene of interest, and the fourth construct comprising a selectable resistance gene to a second antibiotic;

selecting said cell which is resistant to the second antibiotic; and screening said cell which is resistant to the second antibiotic for expression of the gene product of said gene of interest.

8. The cell line of claim 7 wherein said mammalian cell is a BHK-21 cell or a dhfr-minus mutant of CHO.

9. The cell line of claim 7 wherein said herpes simplex virus gene promoter is IE175 promoter region −380 to +26 or the IE110 promoter region −800 to +120.

10. The cell line of claim 7 wherein the selectable resistance gene is selected from the group consisting of genes encoding hygromycin phosphotransferase, aminoglycoside phosphotransferase 3'-II, puromycin acetyl transferase and bleomycin-phleomycin binding protein.

11. The cell line of claim 7 wherein said gene of interest codes for a secreted protein.

12. A The cell line of claim 7 wherein said gene of interest codes for tPA, secreted ICAM, secreted fucosyltransferase, or secreted vascular permeability factor.

13. A cell line which stably expresses a gene product, said cell line comprising:

a first construct which causes the cell to express herpes simplex virus transactivator protein VP16;

a second construct comprising a herpes simplex virus gene promoter that responds to VP16 operably linked to a gene of interest; and a third and fourth construct each comprising a selectable resistance gene to a selectable agent.

14. The cell line of claim 13 wherein said cell line is BHK-21.

15. The cell line of claim 13 wherein said cell is derived from dhfr-minus mutants of CHO cells.

16. The cell line of claim 13 wherein said herpes simplex virus gene promoter is the IE175 promoter region −380 to +26 or the IE110 promoter region −800 to +120.

17. The cell line of claim 15 wherein said cell line is obtained without selecting for dihydrofolate reductase.

18. The cell line of claim 16 wherein the selectable resistance gene is selected from the group consisting of genes encoding hygromycin phosphotransferase, aminoglycoside phosphotransferase 3'-II, puromycin acetyl transferase and bleomycin-phleomycin binding protein.

19. The cell line of claim 13 wherein said gene of interest codes for a secreted protein.

20. The cell line of claim 13 wherein said gene of interest codes for tPA, secreted ICAM, secreted fucosyltransferase, or secreted vascular permeability factor.

\* \* \* \* \*

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 30 base pairs
      (B) TYPE: nucleic acid
      (C) STRANDEDNESS: single
      (D) TOPOLOGY: linear    (ii) MOLECULE TYPE: DNA (genomic)

(xi) SEQUENCE DESCRIPTION: SEQ ID NO:1:

GATCGGATCC AACCCCACCC AATGGACCTC      30

(2) INFORMATION FOR SEQ ID NO:2:

(i) SEQUENCE CHARACTERISTICS:
      (A) LENGTH: 26 base pairs
      (B) TYPE: nucleic acid
      (C) STRANDEDNESS: single
      (D) TOPOLOGY: linear    (ii) MOLECULE TYPE: DNA (genomic)

(xi) SEQUENCE DESCRIPTION: SEQ ID NO:2:

GATCGGATCC GCGCCCCCTA CCCACC      26

(2) INFORMATION FOR SEQ ID NO:3:

(i) SEQUENCE CHARACTERISTICS:

(A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GACCAATTCC AGGATCCCAG GACCCAGT                                              28

(2) INFORMATION FOR SEQ ID NO:4:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GATCGGTACC GCAAACAACA GATGGCTGGC AACTAGA                                    37

(2) INFORMATION FOR SEQ ID NO:5:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GCTAGGATCC CGGGATAGGT TCAGGGAGGC G                                          31

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GATCGGATCC TCAGCCTCGC TATGGCTCCC                                            30

(2) INFORMATION FOR SEQ ID NO:7:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GATCGATCAT GGATCCCTCA TACCGGGGGG AGAG                                       34

(2) INFORMATION FOR SEQ ID NO:8:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GATCCTACCC GTACGACGTT CCGGACTACG CTTCTTAAGA GCTC                              44

(2) INFORMATION FOR SEQ ID NO:9:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:9:

GATCGAGCTC TTAAGAAGCG TAGTCCGGAA CGTCGTACGG GTAG                              44

(2) INFORMATION FOR SEQ ID NO:10:

(i) SEQUENCE CHARACTERISTICS:
            (A) LENGTH: 76 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:10:

GATCCACCAT GAGCCGCCGT CCCGTCCTGC TCCTGCTCCA ACTCCTGGTC GGCCCCGCCA             60

TGGCTAAGCT TGGATC                                                            76

(2) INFORMATION FOR SEQ ID NO:11:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (xi) SEQUENCE DESCRIPTION: SEQ ID NO:11:

Tyr Pro Tyr Asp Val Pro Asp Tyr Ala Ser
1               5                   10

(2) INFORMATION FOR SEQ ID NO:12:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:12:

GATCGACCAT GGCTGCCATA CCCGTACGAC GTTCCGGACT ACGCTTCTAA GCTT                   54